United States Patent
Miljkovic

(10) Patent No.: US 7,959,957 B2
(45) Date of Patent: Jun. 14, 2011

(54) COFFEE CHERRY COSMETIC COMPOSITION AND METHODS

(75) Inventor: Dusan Miljkovic, San Diego, CA (US)

(73) Assignee: VDF Futureceuticals, Inc., Momence, IL (US)

( * ) Notice: Subject to any disclaimer, the term of this patent is extended or adjusted under 35 U.S.C. 154(b) by 0 days.

(21) Appl. No.: 12/631,119

(22) Filed: Dec. 4, 2009

(65) Prior Publication Data

US 2010/0068318 A1    Mar. 18, 2010

Related U.S. Application Data

(62) Division of application No. 10/599,663, filed as application No. PCT/US2004/036630 on Nov. 3, 2004.

(60) Provisional application No. 60/560,865, filed on Apr. 8, 2004, provisional application No. 60/618,900, filed on Oct. 12, 2004.

(51) Int. Cl.
*A01N 65/00* (2009.01)
*A61K 8/02* (2006.01)

(52) U.S. Cl. .................. 424/725; 424/401; 424/776

(58) Field of Classification Search .................. None
See application file for complete search history.

(56) References Cited

U.S. PATENT DOCUMENTS

| | | |
|---|---|---|
| 6,572,915 B1 | 6/2003 | Drunen et al. |
| 2002/0150597 A1 * | 10/2002 | Silva et al. |
| 2002/0160067 A1 | 10/2002 | Zapp et al. |
| 2002/0187239 A1 | 12/2002 | Miljkovic et al. |

FOREIGN PATENT DOCUMENTS

| | | | |
|---|---|---|---|
| FR | 1533371 | | 7/1968 |
| JP | 04145049 | A * | 5/1992 |
| JP | 08208419 | A * | 8/1996 |

OTHER PUBLICATIONS

Suzuki, T et al. J. Sci. ood Agric. (1994); 35: 66-70. Biodegradation of caffeine: Formation of theophylline and theobromine from caffeine in mature *Coffea arabica* fruits.*

Suzuki, T. Annals of Botany (1985); 56: 537-542. Purine alkaloids of the fruits of *Camellia sinensis* L. and *Coffea arabica* L. during fruit development.*

Clifford, M.N. Food Chemistry (1987); 26: 59-69. The influence of coffee bean maturity on the content of chlorogenic acids, caffeine and trigonelline.* http://www.thefreedictionary.com/combining. The Free Dictionary by Fairfax: "combining". Downloaded from world-wide-web on Sep. 13, 2010.*

Sivetz(b) et al. Coffee Technology. 1979, AVI Publishing Company. pp. 74-82, 86, 127-128.*

Bertrand, "Chlorogenci acid content swap during fruit maturation in *Coffea pseudozanguebariae* Qualitative comparison with leaves"; Plant Science; Jul. 22, 2003; pp. 1355-1361; vol. 165; Elsevier Ireland Ltd.

* cited by examiner

*Primary Examiner* — Michele Flood
(74) *Attorney, Agent, or Firm* — Fish & Associates, PC

(57) ABSTRACT

A cosmetic composition comprises a coffee cherry preparation, and most preferably an extract from a sub-ripe quick-dried coffee cherry. Particularly contemplated cosmetic compositions are formulated as a shampoo, lotion, cream, balm, or ointment, and will have at least one of an antioxidant effect, an anti-inflammatory effect, a UV-protective effect, an anti-mutagenic effect, a chemoprotective effect, a scar reducing effect, a skin-lightening effect, a moisturizing effect, a wrinkle reduction effect, and an antibacterial effect.

11 Claims, No Drawings

COFFEE CHERRY COSMETIC COMPOSITION AND METHODS

This application is a divisional application of U.S. application Ser. No. 10/599,663 filed Jul. 20, 2007 which is a US national phase application of PCT/US03/036630 filed Nov. 3, 2004 which claims priority to U.S. Provisional Patent Application Ser. No. 60/560,865 filed Apr. 8, 2004 and U.S. Provisional Patent Application Ser. No. 60/618,900 filed Oct. 12, 2004; and further relates to our International Patent Applications serial numbers PCT/US03/11950 and PCT/US03/11951. This and all other extrinsic materials discussed herein are incorporated by reference in their entirety. Where a definition or use of a term in an incorporated reference is inconsistent or contrary to the definition of that term provided herein, the definition of that term provided herein applies and the definition of that term in the reference does not apply.

FIELD OF THE INVENTION

Cosmetic compositions and methods, especially as they relate to those comprising coffee cherries, coffee cherry preparations, and extracts thereof.

BACKGROUND OF THE INVENTION

Many cosmetic formulations include plant extracts or preparations from one or more plants to achieve a particularly desirable result. Typically, plants used in such formulations are those with known medicinal value. For example, chamomile extracts are frequently used to reduce inflammation, aloe vera extracts are used to relieve skin irritations, and calendula extracts are often used as antiseptic.

Remarkably, most non-medicinal plants, and especially plants that are normally used for food or beverage preparation are commonly absent in cosmetic formulations, and the most notable uses of non-medicinal edible plants in cosmetics includes cucumber for masks, and almonds and apricots for skin peels. In another example, as described in U.S. Pat. App. No. 2004054534, extracts of roasted and unroasted decaffeinated coffee beans are topically used to treat greasy skin. While such extracts are reported to normalize sebaceous gland activity to at least some degree, various disadvantages nevertheless remain. Among other things, and depending on the particular formulation, chemical stability of such extracts may be less than desirable. Alternatively, as taught in U.S. Pat. App. No. 20020187239 and WO 2002062159, the inventors describe use of a plant waste product (e.g., use of coffee cherry pulp from coffee production) as a base material for preparation of a plant extract. However, coffee production typically demands harvest of ripe coffee cherries, which are known to have a substantial level of microbial growth. Consequently, the waste material (i.e. the pulp) is almost invariably and highly contaminated with various mycotoxins and must therefore be detoxified prior to use.

Therefore, while there are numerous cosmetic formulations are known in the art, all or almost all of them suffer from one or more disadvantages, especially where such formulations include a portion of a coffee plant. Consequently, there is still a need to provide improved cosmetic compositions and methods.

SUMMARY OF THE INVENTION

The present invention is directed towards various cosmetic compositions and methods in which the cosmetic composition includes a coffee cherry, or a portion and/or extract thereof.

In one particularly contemplated aspect of the inventive subject matter, the cosmetic composition includes a coffee cherry preparation, and even more preferably a coffee cherry preparation that is prepared from a sub-ripe coffee cherry and/or quick-dried coffee cherry, wherein the sub-ripe coffee cherry is quick-dried such that a mycotoxin level of the coffee cherry is less than 20 ppb for total aflatoxins, less than 10 ppb for total ochratoxins, and less than 5 ppm for total fumonisins. Still further especially preferred coffee cherry preparations are alcoholic and/or aqueous extracts that are prepared from at least two of a bean of the coffee cherry, the pulp, the mucilage, and the hull of the coffee cherry.

Contemplated cosmetic compositions may be formulated in a variety of formulations, and especially preferred formulations include shampoos, lotions, creams, balms, and ointments. Additionally, it is preferred that the cosmetic composition is associated with an information that the composition comprises the coffee cherry preparation, and it is further contemplated that an information may be associated with the composition that the composition has at least one of an antioxidant effect, an anti-inflammatory effect, a UV-preotective effect, an antimutagenic effect, a chemoprotective effect, a scar reducing effect, a skin-lightening effect, a moisturizing effect, a wrinkle reduction effect, and an antibacterial effect.

Depending on the particular nature of the coffee cherry preparation, it should be recognized that such preparations include at least two classes of compounds selected from the group consisting of coffee acids, essential monosaccharides, coffee mucilage polysaccharides, and trigonelline, wherein these classes are present in the extract in an amount of at least 1 wt % total, and more typically at least 5 wt % total. Exemplary contemplated coffee acids include chlorogenic acid, ferulic acid, and caffeic acid, and essential monosaccharides include arabinose, fucose, mannose, xylose, and galactose.

Consequently, a method of marketing a cosmetic composition may comprise a step of providing the cosmetic composition and a further step of providing an information that the composition comprises a coffee cherry preparation. In preferred methods, the coffee cherry preparation comprises an extract of the coffee cherry (most preferably a sub-ripe coffee cherry and/or a quick-dried coffee cherry), and the information is associated with the cosmetic composition (e.g., printed on the container containing the formulation and/or the package containing the container).

Various objects, features, aspects and advantages of the present invention will become more apparent from the following detailed description of preferred embodiments of the invention.

DETAILED DESCRIPTION

The inventors discovered that coffee cherries, portions, and/or extracts thereof can be used in cosmetics, and especially in cosmetic products that are topically applied (e.g., to the skin or hair). It is generally contemplated that any coffee cherry, portion and/or extract thereof is deemed suitable for use herein. However, particularly preferred coffee cherries, portions and/or extracts include those from sub-ripe, ad/or quick-dried coffee cherries, which are particularly low in mycotoxins.

As used herein, the term "coffee cherry" refers to the entire fruit of the coffee tree (*Coffea* spec.) in which the exocarp and the outer mesocarp (i.e., the pulp) surround the inner mesocarp (i.e. the mucilage) and endocarp (i.e., the hull), which in turn surround the seeds (i.e., the beans). Thus, the term coffee cherry specifically refers to a whole coffee cherry, which may or may not include the stem of the cherry.

The term "sub-ripe coffee cherry" refers to a coffee cherry that has not yet reached the ripe stage, which is generally characterized by susceptibility to or presence of a fungal infection and/or presence of mycotoxins. Thus, a sub-ripe coffee cherry is at a ripeness stage in which the coffee cherry—when quick-dried—will exhibit mycotoxin levels that are below 20 ppb for total aflatoxins, below 5 ppm for total fumonisins, below 5 ppm for total vomitoxins, and below 5 ppb for ochratoxins. Quick-dried coffee cherries are typically dried within 0-48 hours (and more preferably between 6-24 hours) of the harvest such that the residual water content is no higher than 20% (wt/wt), and more typically no higher than 6-12% (wt/wt).

Viewed from an other perspective, sub-ripe coffee cherries will typically exhibit at least some green color (at least 5%, more typically at least 10%) and will typically be free of any surface defects (e.g., blemishes, cuts, and/or holes covering an area of less than 5% of the cherry). Sub-ripe coffee cherries may also be characterized in that they will remain on the coffee tree for a subsequent round of picking where the coffee cherries are hand picked and used for the production of coffee beans. Alternatively, a color sorting machine (e.g., CCD equipment) may be employed to identify and select sub-ripe coffee cherries on a quantitative color basis where the coffee cherries are mass-harvested and automatically sorted.

It should further be appreciated that while many of the following contemplated aspects and examples employ coffee cherries in a sub-ripe state, completely ripe coffee cherries are also deemed suitable herein, and especially where such ripe coffee cherries are substantially devoid of surface damage (i.e., no more than 5% of surface area) and/or microbial infection (i.e., infestation that results in mycotoxin levels of less than 20 ppb for total aflatoxins, less than 5 ppm for total fumonisins, less than 5 ppm for total vomitoxins, and less than 5 ppb for ochratoxins on a dry weight basis). Thus, all contemplated cosmetic products and/or coffee cherries may comprise completely ripe as well as sub-ripe coffee cherries in varying proportions. For example, suitable proportions include 100% ripe to 0% sub-ripe, preferably 90% ripe to 10% sub-ripe, more preferably 75% ripe to 25% sub-ripe, even more preferably 50% ripe to 50% sub-ripe, and most preferably less than 25% ripe to more than 75% sub-ripe.

As further used herein, the term "quick-dried" coffee cherry means that the whole coffee cherry is dried under a protocol that limits growth of molds, fungi, and/or yeast to an extent such that the dried coffee cherry will exhibit mycotoxin levels that are below 20 ppb for total aflatoxins, below 5 ppm for total fumonisins, below 5 ppm for total vomitoxins, and below 5 ppb for ochratoxins. Quick-dried coffee cherries are typically dried within 0-48 hours (and more preferably between 6-24 hours) of the harvest such that the residual water content is no higher than 20% (wt/wt), and more typically no higher than 6-12% (wt/wt). Suitable drying processes (which may or may not result in a quick-dried coffee cherry of portion thereof) include air-drying, sun-drying, spray-drying, freeze-drying, etc.

As still further used herein, the term "mycotoxin" refers to any toxic product formed in a mold, fungus, and/or yeast that exhibits significant toxicity to a human or animal when ingested. Specifically contemplated mycotoxins include aflatoxins (and particularly B1, B2, G1, and G2), fumonisins (and particularly B1, B2, and B3), ochratoxin, deoxynivalenol (DON, vomitoxin), T-2 toxin, and zearalenone. The term "total aflatoxins" therefore refers to the sum of all aflatoxin variants, the term "total fumonisins" refers to the sum of all fumonisin variants, and the term "total ochratoxins" therefore refers to the sum of all ochratoxin variants.

Exemplary preparations of suitable coffee cherries, portions and/or extracts of are described in our commonly owned and copending International patent applications with the serial numbers PCT/US03/11950 (with the title "Low-Mycotoxin Coffee Cherry Products") and PCT/US03/11951 (with the title "Methods for Coffee Cherry Products"), which are specifically incorporated by reference herein. Further, while it is generally preferred that the coffee cherry products are low, or even devoid in mycotoxins, it should be recognized that for topical use, the allowed and/or tolerated quantity of mycotoxins may be higher than required for nutritional products. Thus, it is generally preferred that contemplated coffee cherry preparations are made from sub-ripe and/or quick-dried coffee cherries or from a batch of coffee cherries that includes at least a fraction (e.g., at least 10%, more typically at least 20%, most typically at least 50%) of sub-ripe and/or quick-dried coffee cherries.

In generally preferred cosmetic formulations, the coffee cherry preparation may be in various forms suitable for compounding into a cosmetic product, or may even be formulated for direct application without further compounding. Therefore, contemplated coffee cherry preparations may be prepared as a mechanically processed material (e.g., freeze-dried powder, or otherwise comminuted and dehydrated material, or liquid obtained from pressed coffee cherries). It should further be appreciated that the coffee cherries may be (e.g., after a step of mechanical processing) chemically processed, and particularly suitable chemical processing steps include solvent extraction or fractionation. For example, coffee cherries may be comminuted and extracted with an aqueous and/or alcoholic solvent to obtain a solution enriched in one or more desirable components (and/or to obtain a material depleted of one or more undesired components). So prepared extracts can further be refined and/or enriched in a specific component using chromatographic methods (e.g., ion exchange, size exclusion, or filtration), or addition of a component or fragment of the coffee cherry. Depending on the desired component(s), it should further be recognized that the extracts may also be prepared from selected portions of a coffee cherry (e.g., at least one or more of the bean of the coffee cherry, the pulp, the mucilage, and/or the hull of the coffee cherry).

It should be noted that more than 50 wt % of the dry matter of a sub-ripe coffee berry is represented by carbohydrates, and especially polysaccharides. The remainder is comprised of various proteins (about 10 wt % to 12 wt %), saponifiable lipids (about 10 wt % to 18 wt %), unsaponifiable lipids (about 10 wt %), and various other lipophilic components, including phytosterols, tocopherols, diterpenic alcohols (e.g. cafestol, kahweol, kauranic derivatives), etc. Coffee cherries further comprise various phenolic acids (typically about 5 wt %), with typical representatives being ferulic acid, quinic acid, caffeic acid, and chlorogenic acid. Caffeine may be present between about 0.5 wt % to about 2 wt % and even higher.

Depending on the particular nature of the preparation of the coffee cherry (extract), contemplated preparations and/or extracts will therefore include varying amounts of coffee acids (e.g., chlorogenic acid, ferulic acid, and caffeic acid), essential monosaccharides (e.g., glucose, galactose, arabinose, mannose, xylose, fucose, N-acetylgalactosamine, N-acetylglucosamine, and N-acetylneuraminic acid), coffee mucilage polysaccharides, and/or trigonelline. However, it is typically preferred that (at least two of) the coffee acids, essential monosaccharides, coffee mucilage polysaccharides, and/or trigonelline are present in the cosmetic composition, preparation, or extract in an amount of at least 1 wt % total, more preferably 2-5 wt % total, and most preferably between 5 and 20 wt % total.

With respect to contemplated cosmetic formulations, it is generally preferred that the cosmetic formulation is topically applied to the skin, nails, and/or hair. Consequently, the particular composition and manner of application may vary considerably, and all known cosmetic compositions and/or formulations are considered suitable for use herein. For example, suitable cosmetic products include gels, creams, mousses, ointments, liquids (sprayable or otherwise applied) lipstick formulations, etc., all of which may be used as a cleaning agent, a skin care agent, and/or functional cosmetic. There are numerous formulations for cosmetic use known in the art (see e.g., Cosmetic and Toiletry Formulations Volume 8 by Ernest W. Flick; Noyes Publications; 2nd edition, Jan. 15, 2000; ISBN: 0815514549), and all of them are deemed suitable for use herein.

In most instances, it is contemplated that the cosmetic composition will include the coffee cherry preparation in an amount of between about 0.1 wt % to about 80 wt %, more preferably in an amount of between about 1 wt % to about 40 wt %, and most preferably in an amount of between about 5 wt % to about 20 wt %. However, where the coffee cherry preparation is highly concentrated, lower quantities are also contemplated. It is still further contemplated that the cosmetic compositions according to the inventive subject matter may further include additional agents, including detergents, antioxidants, vitamins, minerals (e.g., complexed boron), fragrance, plant hormones, alpha hydroxy acids, acetylated compounds (e.g., N-acetyl cysteine), etc.

In still further contemplated aspects, it should be recognized that the coffee cherries (which may be sub-ripe and/or ripe) may be directly used in cosmetic formulations without a step of drying. For example, such coffee cherries may be comminuted, powderized, or macerated into a paste or purée, which is then included into a cosmetic formulation. Alternatively, the coffee cherries may also be pressed to obtain a coffee cherry juice or juice concentrate, which is then included into the cosmetic formulation. It should further be appreciated that while such materials from non-dried coffee cherries are preferably included into a cosmetic formulation, other uses, and especially uses in nutritional applications are also expressly contemplated herein. For example, such juices, purées, and other material may be included into a snack bar, beverage, or other edible material at various concentrations (e.g., between about 0.01 wt % to about 99.9 wt %, more typically between 0.1 wt % to about 50 wt %, most typically between 1 wt % to about 20 wt %), and particularly suitable food products and uses are described in our International Patent Applications with the serial numbers PCT/US03/11950 and PCT/US03/11951, which are incorporated by reference herein. Additionally contemplated uses include use of contemplated coffee cherry preparations as anti-oxidant in a composition of matter, wherein the concentration of the coffee cherry preparation is typically between about 0.01 wt % to about 99.9 wt %, more typically between 0.1 wt % to about 50 wt %, most typically between 1 wt % to about 20 wt % of the entire composition.

Still further, it should be noted that contemplated compositions and methods may also employ plant extracts from plants other than a coffee tree, and plants that comprise (preferably at least two of) chlorogenic acid, caffeic acid, and ferulic acid are especially preferred. Most preferably, the chlorogenic acid, caffeic acid, and ferulic acid are present in an amount of at least 0.1 wt % (or 0.5 wt % to about 5 wt %, and even higher) in such alternative plants.

While not limiting to the inventive subject matter, the inventors contemplate that the cosmetic compositions presented herein may exhibit numerous advantages for topical use. Among other things, the inventors contemplate that numerous coffee cherry components complement each other in their potential various ingredients (e.g., ferulic acid, caffeic acid, or chlorogenic acid) may act as UV protectant, and/or as antioxidant. In another example, the inventors contemplate that coffee cherry products include various polysaccharides, and especially mucilage polysaccharides, which may have beneficial effect of the skin (e.g., via hydration or other effect). Thus, contemplated beneficial effects of the cosmetic compositions according to the inventive subject matter include improved skin tone, increased exfoliation, keratinolytic effect, reduction in wrinkles, reduction in biological and/or apparent ageing, reduction in hyperpigmentation (e.g., melasma, due to UV exposure, age-related, etc.), reduction in direct and indirect oxidative damage (antioxidant properties), reduction in irritation and/or inflammation, and/or improved feel (e.g., increased smoothness).

Consequently, the inventors contemplate that the cosmetic compositions according to the inventive subject matter can be marketed in association with an information that the cosmetic composition comprises a coffee cherry preparation (which is preferably prepared from a sub-ripe and/or quick-dried coffee cherry). There are numerous manners in which the association may be provided, and particularly preferred associations include physical association in which the information is printed on the container that contains the composition, or in which the information is printed on a package that includes the container. Similarly, the information may also be provided via a sales display and/or a brochure or publication. Alternatively, or additionally, the information may not only be provided in a written or printed form, but may also be displayed in a graphic format (e.g., via Internet) and/or displayed as a commercial advertisement or infomercial.

In especially contemplated aspects, the information will associate the coffee cherry preparation and/or the cosmetic composition comprising the coffee cherry preparation with a desirable effect. Among other contemplated effects, the coffee cherry preparation and/or the cosmetic composition comprising the coffee cherry preparation has at least one of an antioxidant effect, an anti-inflammatory effect, a UV-protective effect, an antimutagenic effect, a chemoprotective effect, a scar reducing effect, a skin-lightening effect, a wrinkle reduction effect, a moisturizing effect, and an antibacterial effect.

EXAMPLES

The following examples are provided to enable a person of ordinary skill in the art to make and use compositions according to the inventive subject matter and to illustrate exemplary compositions and methods generally described herein.

Harvest of Whole Coffee Cherries

The ripeness of the coffee cherries was determined by visually estimating the amount of green and red color (or yellow, where applicable) of the whole cherries. As the cherries ripen, the green cherries will typically increase in size and subsequently develop increasing amounts of red color. For the present examples, the coffee cherries were collected at four stages of ripeness: Completely, or almost completely green (unripe; typically less than 5% of the coffee cherry red or yellow), primarily green with some red (semi-ripe, stage 1; typically less than 25% of the coffee cherry red or yellow), primarily red with some green (semi-ripe, stage 2; typically less than 25% of the coffee cherry green), and unbroken, unblemished red (almost ripe; typically less than 10% of the coffee cherry green; area of blemishes, cuts, or otherwise broken surface less than 5%). As much as possible, whole, unbroken and uncut cherries were collected.

Quick-Drying of the Whole Coffee Cherries

Whole coffee cherries for sample extraction were prepared by drying the cherries within 1-12 hours after harvest on separate trays of an air dryer according to the following procedure. Coffee cherries (400-600 g) were weighed into beakers and washed two times with tap water, followed by a single wash with distilled water. The so washed coffee cherries were placed on a tray of an air dryer to drain, and then dried at 150-160° F. for 16-18 hours to constant weight. Drying was stopped when the weight at two consecutive one-hour intervals differed by less than 1 g. Typical yields of dried whole cherry were 160-220 g. Further analysis indicated 6-12% residual water content in the dried cherry.

Mycotoxin Analysis

In order to determine the viability of the whole coffee cherry at the unripe, semi-ripe, and almost ripe stages (see above) for use in a nutritional product (and especially for use in tea), the level of selected mycotoxins was measured and compared against comparative products and red, ripe coffee cherry by-product from coffee production. As can be clearly seen in Table 1 below, quick-dried coffee cherries of all sub-ripe harvest stages had a mycotoxin level below the detection limit of 1 ppb (as measured for aflatoxin and ochratoxin).

The mycotoxin concentration was determined in an independent laboratory by both ELISA and HPLC analysis. Based on the below results, the inventors conclude that all samples from the different sub-ripe harvest stages are suitable for direct use in a cosmetic composition for human topical use. In contrast, a typical by-product during coffee production (predominantly consisting of pulp, mucilage, and hull from coffee cherries) from ripe cherries of red color with blemishes (typically greater than 20% of the cherry surface) had a substantial content in both aflatoxins and ochratoxins.

TABLE 1

| RIPENESS | COLOR | AFLATOXIN | OCHRATOXIN |
| --- | --- | --- | --- |
| Unripe, quick-dried | Green | <1 ppb | <1 ppb |
| Semi-ripe Stage 1, quick-dried | Mostly green with some red | <1 ppb | <1 ppb |
| Semi-ripe Stage 2, quick-dried | Mostly red with some green | <1 ppb | <1 ppb |
| Almost ripe, quick-dried | Red, Blemished Area <5% | <1 ppb | <1 ppb |
| Ripe (by-product of Coffee Production) | Red, Blemished Area >20% | >200 ppb | >500 ppb |

Polyphenol (PP), Chlorogenic Acid (CG), and Caffeine (CF) Analysis for Quick-Dried Sub-Ripe Whole Coffee Cherries In a further series of experiments, the levels of total polyphenols, chlorogenic acid, and caffeine from quick-dried whole coffee cherry at various sub-ripe stages were measured and compared against green and roasted coffee beans. Table 2 summarizes the results of this analysis.

Interestingly, while the polyphenol (PP) level of quick-dried coffee cherries of all sub-ripe harvest stages was somewhat less than the level of green or roasted coffee beans, significant quantities of polyphenols in quick-dried sub-ripe coffee cherries still remain. Similarly, the chlorogenic acid (CG) content of quick-dried whole coffee cherry at various sub-ripe stages remained at substantial high levels as compared to roasted coffee, but was somewhat lower as compared to green beans. The caffeine (CF) level of quick-dried coffee cherries of all sub-ripe harvest stages was substantially within the caffeine level of green and roasted coffee beans (It should be pointed out that all data given are on a dry matter basis and are not normalized to the dry weight of the bean).

Polyphenol analysis: Dried whole coffee cherry (or green beans or roasted beans) (1.00 g) were ground in a rotating steel knife coffee grinder for 30 seconds to produce a ground sample. The ground sample was added to 100 mL distilled water and the resulting mixture heated to boiling in an Erlenmeyer flask for 30 minutes. The heat was removed and the mixture allowed to cool to room temperature. The resulting suspension was transferred to a 100 mL graduated cylinder and water added to bring the volume to 100 mL. The mixture was then transferred back to the Erlenmeyer flask, stirred briefly, and the solids allowed to settle. An aliquot (~3 mL) of the supernatant solution was filtered through an 0.45 μm Acrodisc filter, and the resulting clear solution was diluted 1:10 with distilled water using a volumetric flask (1.00 mL diluted with 9.00 mL distilled water).

The Folin-Ciocalteu method was used to measure the polyphenol content of the diluted solution as follows. One mL of the diluted solution was added to a test tube, mixed with 1 mL of 0.2N Folin-Ciocalteu's Phenol reagent (Sigma solution, 2N, diluted 1:10 with water), and allowed to stand 5 minutes at room temperature. One mL of 1N $NaHCO_3$ was added and the reaction mixture left at room temperature for 2 hours. The polyphenol level was determined using a UV-visible spectrophotometer standardized against catechin, at λmax=750 nm against distilled water as blank.

Chlorogenic acid: Determination of chlorogenic acid was done using HPLC separation of the filtered clear solution prepared above using standard analytical and separation protocols well known in the art. Similarly, determination of caffeine was done using HPLC separation of the filtered clear solution prepared above using standard analytical and separation protocols well known in the art (for exemplary protocols see e.g., Bispo M. S., et al. in J. Chromatogr. Sci.; 2002, January; 40(1):45-8, or Nakakuki, H. et al. in J. Chromatogr. A.; 1999, Jul. 2; 848(1-2):523-7).

TABLE 2

| RIPENESS | COLOR | % PP | % CG | % CF | CG/CF |
| --- | --- | --- | --- | --- | --- |
| Unripe, quick-dried | Green | 3.80 | 2.64 | 1.03 | 2.56 |
| Semi-ripe stage 1, quick-dried | Mostly green with some red | 3.28 | 2.70 | 1.00 | 2.70 |
| Semi-ripe stage 2, quick-dried | Mostly red with some green | 3.54 | 2.00 | 0.70 | 2.86 |
| Almost ripe, quick-dried | Red, Blemished Area <5% | 3.35 | N/D | N/D | N/D |
| Green Coffee beans | Green | 4.58 | 3.31 | 0.95 | 3.48 |
| Roasted Coffee beans | Brown | 3.93 | 0.50 | 1.20 | 0.42 |

Preparation of an Aqueous Coffee Cherry Extract

Quick-dried sub-ripe coffee cherry were ground in several batches in a rotating steel knife coffee grinder for 10-30 seconds to produce a ground sample. To the ground sample (20.0 g) will be added 80 mL boiling distilled water and the resulting mixture will be allowed to cool off in an Erlenmeyer flask to room temperature. The solids will be filtered and the filtrate will be freeze dried and powderized. A second batch will be prepared as above using hot 40 vol % ethanol in water as a solvent, and the filtrate will be freeze dried and powderized.

Both powders will be resuspended in water to form a 10 wt % solution, respectively, and the solution will be again filtered to remove undissolved matter. The so obtained coffee cherry preparation will be then added to the cosmetic base formulations in proportions as given below:

| Body Lotion (Oil-in-water) | | |
|---|---|---|
| a) | PEG-7 hydrogenated castor oil | 2.00% |
| | PEG-20 glyceryl laurate | 1.00% |
| | cocoglycerides | 3.00% |
| | cetearyl alcohol | 1.00% |
| | cetearyl isononanoate | 4.00% |
| | octyl stearate | 4.00% |
| | phenoxyethanol, methylparaben, ethylparaben, butylparaben, propylparaben, isobutylparaben | 0.30% |
| b) | water, distilled | 73.40% |
| | phenoxyethanol, methylparaben, ethylparaben, butylparaben, propylparaben, isobutylparaben, | 0.30% |
| | glycerin | 3.00% |
| c) | Coffee Cherry Extract | 5.00% |
| d) | acrylamides copolymer, mineral oil | 3.00% |

C13-C14 isoparaffin, polysorbate 85

Mixture a) is melted at approximately 70° C. and mixture b) is heated to approximately 70° C. and added to mixture a) while stirring. Stirring is continued until the lotion has cooled down to approximately 30° C. Then c) and d) are added while stirring, and the lotion is homogenized.

| Gel-Lotion | | |
|---|---|---|
| a) | acrylamides copolymer, mineral oil, C13-14 isoparaffin, polysorbate 85 | 5.00% |
| | myreth-3 myristate | 4.00% |
| b) | water, distilled | 85.00% |
| | phenoxyethanol (and) methylparaben (and) ethylparaben (and) butylparaben (and) propylparaben (and) isobutylparaben | 0.50% |
| | xanthan gum | 0.50% |
| c) | Coffee Cherry Extract | 5.00% |

Mixture a) is dissolved at approximately 50° C. Mixture b) is dispersed at room temperature and added to a) while stirring. Then, composition c) is added while stirring.

| Oil-in-water Cream | | |
|---|---|---|
| a) | cetearyl alcohol (and) ceteareth-20 | 8.00% |
| | cocoglycerides | 2.00% |
| | cetearyl alcohol | 2.00% |
| | dicaprylyl ether | 8.00% |
| | oleyl erucate | 7.00% |
| | phenoxyethanol, methylparaben, ethylparaben, butylparaben, propylparaben, isobutylparaben | 0.30% |
| b) | water, distilled | 62.40% |
| | phenoxyethanol, methylparaben, ethylparaben, butylparaben, propylparaben, isobutylparaben | 0.30% |
| | glycerin | 5.00% |
| c) | Coffee Cherry Extract | 5.00% |

Mixture a) is melted at approximately 70° C. and mixture b) is heated to approximately 70° C. and added to mixture a) while stirring. Stirring is continued until the cream has cooled down to approximately 30° C. Then, composition c) is added while stirring and the cream is homogenized.

| Water-in-oil Cream | | |
|---|---|---|
| a) | diisostearoyl polyglyceryl-3 dimer dilinoleate | 3.00% |
| | beeswax | 0.60% |
| | castor oil, hydrated | 0.40% |
| | paraffinum subliquidum | 5.00% |
| | isohexadecane | 10.00% |
| | PPG-15 stearyl ether | 2.00% |
| | dimethicone | 0.50% |
| | phenoxyethanol, methylparaben, ethylparaben, butylparaben, propylparaben, isobutyparaben | 0.30% |
| b) | water, distilled | 68.40% |
| | phenoxyethanol, methylparaben, ethylparaben, butylparaben, propylparaben, isobutylparaben | 0.30% |
| | glycerin | 3.00% |
| | $MgSO_4 \cdot 7H_2O$ | 1.00% |
| c) | Coffee Cherry Extract | 5.00% |
| d) | silica dimethyl silylate | 0.50% |

Mixture a) is heated to approximately 80° C., mixture b) is brought to 80° C. and added to a) while stirring. Stirring is continued until the cream has cooled down to approximately 30° C., then c) and d) are added, and the cream is homogenized.

| Shampoo | |
|---|---|
| Sodium polyoxyethylene lauryl ether sulfate | 15.0% |
| Alkyl polyglucoside | 4.0% |
| N-ethanol-N-methyl dodecanoic acid amide | 3.0% |
| EDTA-$Na_2$ | 0.3% |
| Malic acid to adjust pH to 6.0 | q.s. |
| Preservative | 0.5% |
| Coffee Cherry Extract | 10.0% |
| Purified water | balance |
| Total | 100.0% |

All ingredients are mixed together and the volume is brought to about 90 ml. The pH is then adjusted and the volume is finally adjusted to 100 ml (all percentages are weight %).

| Body Wash | |
|---|---|
| Sodium polyoxyethylene lauryl ether sulfate | 16.0% |
| Sodium polyoxyethylene | 5.0% |
| N-ethanol-N-methyl palm kernel oil fatty acid amide | 2.5% |
| Glycerin | 3.0% |
| Cationized cellulose | 0.1% |
| Ethylene glycol distearate | 3.0% |

-continued

| Body Wash | |
| --- | --- |
| EDTA-Na$_2$ | 0.3% |
| Citric acid to adjust pH to 5.7 | q.s. |
| Preservative | 0.5% |
| Coffee Cherry Extract | 7.5% |
| Purified water | balance |
| Total | 100.0 |

All ingredients are mixed together and the volume is brought to about 90 ml. The pH is then adjusted and the volume is finally adjusted to 100 ml (all percentages are weight %).

| Face Wash | |
| --- | --- |
| Sodium polyoxyethylene lauryl ether sulfate | 20.0% |
| N-ethanol-N-methyl dodecanoic acid amide | 4.8% |
| Glycerin | 3.0% |
| Hydroxyethyl cellulose | 0.3% |
| Ethylene glycol distearate | 1.5% |
| EDTA-Na$_2$ | 0.3% |
| Citric acid to adjust pH to 6.0 | q.s. |
| Preservative | 0.5% |
| Coffee Cherry Extract | 10.0% |
| Purified water | balance |
| Total | 100.0 |

All ingredients are mixed together and the volume is brought to about 90 ml. The pH is then adjusted and the volume is finally adjusted to 100 ml (all percentages are weight %).

Thus, specific embodiments and applications of low-mycotoxin coffee cherry products have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

What is claimed is:

1. A method of producing a cosmetic product comprising providing or preparing a crude extract of whole coffee cherries, wherein the whole coffee cherries are optionally quick-dried whole coffee cherries; and combining the crude extract with a cosmetic composition, wherein the optionally quick-dried whole coffee cherries are prepared by drying whole coffee cherries to a residual water content of equal or less than 20 weight (wt.) % within 48 hours after harvesting the whole coffee cherries, wherein the whole coffee cherries are (1) sub-ripe whole coffee cherries having between 5% green color and 25% green color or (2) whole coffee cherries having less than 10% green color and having surface defects that cover less than 5% of the surface area of the whole coffee cherries, and wherein the crude extract is an aqueous crude extract or a water/organic solvent crude extract.

2. The method of claim 1 wherein the whole coffee cherries have less than 10% green color and have surface defects that cover less than 5% of the surface area of the cherries.

3. The method of claim 1, wherein the whole coffee cherries are sub-ripe coffee cherries having between 5% green color and 25% green color.

4. The method of claim 1, wherein the crude extract, prior to combining the crude extract with the cosmetic composition, is partially enriched in at least one of polyphenols, trigonelline, essential monosaccharides, and mucilage polysaccharides from whole coffee cherries.

5. The method of claim 4, wherein at least one of the polyphenols, trigonelline, essential monosaccharides, and mucilage polysaccharides from whole coffee cherries is present in the cosmetic product in an amount between 5 and 20 wt. %.

6. The method of claim 1 wherein the crude extract is an aqueous crude extract.

7. The method of claim 1 wherein the crude extract is a water/organic solvent crude extract.

8. The method of claim 1 wherein the crude extract is a concentrate prepared by at least partial removal of water or water/organic solvent from the crude extract.

9. The method of claim 1 wherein the whole quick-dried coffee cherries have less than 20 parts per billion (ppb) total aflatoxins, less than 10 ppb total ochratoxins, and less than 5 parts per million (ppm) total fumonisins without a step of mycotoxin detoxification.

10. The method of claim 1 wherein the extract provides at least one of reduced oxidative damage in skin, increased exfoliation, and keratinolytic effect.

11. The method of claim 1 wherein the extract provides at least one of a chemoprotective effect, a scar reducing effect, a skin-lightening effect, a moisturizing effect, and an antibacterial effect.

* * * * *